(12) United States Patent
Chung et al.

(10) Patent No.: US 11,654,097 B2
(45) Date of Patent: May 23, 2023

(54) PEPTIDE HAVING ACTIVITIES OF SKIN WHITENING AND USES THEREOF

(71) Applicant: CAREGEN CO., LTD., Anyang-si (KR)

(72) Inventors: Yongji Chung, Gunpo-si (KR); Eun Mi Kim, Yongin-si (KR); Eung Ji Lee, Anyang-si (KR); Jan Di Kim, Seoul (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 16/625,865

(22) PCT Filed: Oct. 10, 2019

(86) PCT No.: PCT/KR2019/013266
§ 371 (c)(1),
(2) Date: Mar. 11, 2020

(87) PCT Pub. No.: WO2021/033831
PCT Pub. Date: Feb. 25, 2021

(65) Prior Publication Data
US 2022/0183949 A1 Jun. 16, 2022

(30) Foreign Application Priority Data
Aug. 20, 2019 (KR) .......... 10-2019-0101880

(51) Int. Cl.
| A61K 38/00 | (2006.01) |
| A61K 8/64 | (2006.01) |
| A61Q 19/02 | (2006.01) |
| C07K 7/06 | (2006.01) |
| A61P 17/02 | (2006.01) |

(52) U.S. Cl.
CPC .............. *A61K 8/64* (2013.01); *A61Q 19/02* (2013.01); *C07K 7/06* (2013.01)

(58) Field of Classification Search
CPC .......... A61K 38/00; A61K 8/64; A61P 17/02; A61Q 19/02; C07K 7/06
See application file for complete search history.

(56) References Cited

U.S. PATENT DOCUMENTS

| 7,057,013 B1 | 6/2006 | Ezquerro Saenz et al. |
| 8,344,211 B2 * | 1/2013 | Alexandrov ........... A23K 10/30 435/320.1 |
| 8,969,296 B2 | 3/2015 | Chung et al. |
| 9,012,723 B2 * | 4/2015 | Guo ............... C12N 15/8261 800/312 |
| 10,080,775 B2 | 9/2018 | Chung et al. |
| 10,188,694 B2 | 1/2019 | Cho et al. |
| 2019/0382445 A1 | 12/2019 | Boo et al. |
| 2020/0148721 A1 | 5/2020 | Chung et al. |

FOREIGN PATENT DOCUMENTS

| EP | 3412275 A1 | 12/2018 |
| KR | 10-2008-0094296 A | 10/2008 |
| KR | 10-2017-0073821 A | 6/2017 |
| KR | 10-2017-0113156 A | 10/2017 |
| KR | 10-2017-0139259 A | 12/2017 |
| KR | 10-2018-0128553 A | 12/2018 |
| WO | WO-2016/034541 A1 | 3/2016 |

OTHER PUBLICATIONS

UniProt A0A662ALR8_9BACT, pp. 1-4. Last updated Apr. 22, 2020. (Year: 2020).*
UniProt A0A4D7DSR4_9SPHN, pp. 1-3. Last updated Jul. 31, 2019. (Year: 2019).*
Hyperpigmentation from Merck Manual, pp. 1-4. Accessed Jul. 11, 2022. (Year: 2022).*
Office Action dated Jan. 7, 2021, for Korean Patent Application 10-2019-010880, Chung et al., "Peptide having activities of skin whitening and uses thereof," filed Aug. 20, 2019 (4 pages).
International Search Report dated Jun. 19, 2020 for PCT International Application No. PCT/KR2019/013266, Chung et al., "Peptides Having Activities of Skin Whitening and Uses Thereof," filed Oct. 10, 2019 (5 pages).
Extended European Search Report dated Dec. 15, 2021, for European Patent Application No. 19930166.4, Chung et al., "Peptide having Skin Whitening Activity and Use Thereof," filed Oct. 10, 2019 (10 pages).
Ochiai et al., "Rice Bran Protein as a Potent Source of Antimelanogenic Peptides with Tyrosinase Inhibitory Activity," J. Nat. Prod. 79(10):2545-2551 (2016).

* cited by examiner

*Primary Examiner* — Julie Ha
(74) *Attorney, Agent, or Firm* — Clark & Elbing LLP; Susan M. Michaud

(57) ABSTRACT

Provided are a peptide having skin-whitening activity and use thereof, and a peptide consisting of an amino acid sequence of SEQ ID NO: 1, SEQ ID NO: 2, or SEQ ID NO: 3, a skin-whitening composition including the peptide, a cosmetic composition including the skin-whitening composition, and a pharmaceutical composition for preventing or treating a melanin hyperpigmentation disease, the pharmaceutical composition including the skin-whitening composition.

18 Claims, 5 Drawing Sheets

Specification includes a Sequence Listing.

PEPTIDE HAVING ACTIVITIES OF SKIN WHITENING AND USES THEREOF

SEQUENCE LISTING

The instant application contains a Sequence Listing which has been submitted electronically in ASCII format and is hereby incorporated by reference in its entirety. Said ASCII copy, created on Dec. 20, 2019 is named 51401-017001_Sequence_Listing_12.20.19_ST25 and is 3,536 bytes in size.

TECHNICAL FIELD

The present disclosure relates to a peptide having skin-whitening activity and use thereof.

BACKGROUND ART

Factors that determine skin color basically include melasma, freckles, and tanning due to UV exposure, except for differences by race, region, gender, and age, and also include general pigmentation, acne, scars, keratin distribution, blood circulation, stress, health conditions, etc. Among the factors, pigmentation is known as a major factor that determines skin color.

Pigments that affect skin color include melanin, melanoid, carotene, hemoglobin, carotenoid, etc., and various colors of the skin, hair, and eyes are determined by these pigments. Among them, the most important pigment to determine skin color is melanin, and specifically, skin color is determined by the amount and distribution of melanin. Melanin is produced in cells called melanocytes under the skin's epidermis, and is transferred to and pushed away from the stratum corneum by the skin metabolism. Regardless of the skin color, the number of melanocytes is almost the same, but the difference in the skin color is only attributed to the amount, type, and distribution of melanin.

In the skin, tyrosine is converted to DOPA by an enzyme in the human body, called tyrosinase, and a series of oxidation processes finally produce melanin, which is a dark brown polymer. When more melanin is produced than necessary, hyperpigmentation such as melasma, freckles, spots, etc. may be caused, which are cosmetically bad results. Recently, the leisure population has increased and more people enjoy outdoor activities, and thus, there is an increasing demand to prevent melanin pigmentation caused by ultraviolet rays.

Under this technical background, various studies have been conducted on the development of a whitening agent that prevents excessive melanin production through mechanisms such as inhibition of melanocyte activity, inhibition of tyrosinase activity, etc. (Korea Patent Publication No. 10-2019-0109722), but satisfactory results have not yet been obtained.

DESCRIPTION OF EMBODIMENTS

Technical Problem

An aspect provides a peptide consisting of an amino acid sequence of SEQ ID NO: 1, SEQ ID NO: 2, or SEQ ID NO: 3.

Another aspect provides a skin-whitening composition including the peptide consisting of an amino acid sequence of SEQ ID NO: 1, SEQ ID NO: 2, or SEQ ID NO: 3 as an active ingredient.

Still another aspect provides a cosmetic composition including the skin-whitening composition.

Still another aspect provides a pharmaceutical composition for preventing or treating a melanin hyperpigmentation disease, the pharmaceutical composition including the skin-whitening composition.

Other objects and advantages of the present disclosure will become more fully apparent from the following detailed description of the embodiments, the appended claims and the accompanying drawings. Since contents that are not described in the present specification may be sufficiently recognized and inferred by those skilled in the art or similar art, a description thereof will be omitted.

Solution to Problem

Each description and embodiment disclosed in this application may be applied to other descriptions and embodiments. That is, all combinations of various elements disclosed in this application fall within the scope of the present application. Further, the scope of the present application is not limited by the specific description described below.

An aspect provides a peptide consisting of an amino acid sequence of SEQ ID NO: 1, SEQ ID NO: 2, or SEQ ID NO: 3.

As used herein, the term "peptide" may refer to a linear molecule formed by binding of amino acid residues to each other by peptide bonds. The peptide may be prepared according to a chemical synthesis method known in the art, in particular, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891). The present inventors have made intensive efforts to develop a peptide having biologically effective activity, and as a result, they have identified the peptide consisting of an amino acid sequence of SEQ ID NO: 1, SEQ ID NO: 2, or SEQ ID NO: 3. Here, the biologically effective activity may exhibit one or more characteristics selected from (a) inhibition of melanin production; (b) inhibition of tyrosinase activity; and (c) inhibition of Rab27a, Mlph, myosin VA, MITF, tyrosinase, or TRP1 expression. Therefore, the peptide may be used for whitening the skin and for preventing or treating a melanin hyperpigmentation disease.

The peptide may be bound with a protecting group at the N- or C-terminus thereof to obtain chemical stability, enhanced pharmacological properties (half-life, absorbency, titer, potency, etc.), altered specificity (e.g., broad biological activity spectrum), and reduced antigenicity. In a specific embodiment, the N-terminus of the peptide may be bound with any one protecting group selected from the group consisting of an acetyl group, a fluoreonylmethoxycarbonyl group, a formyl group, a palm itoyl group, a myristyl group, a stearyl group, a butoxycarbonyl group, an allyloxycarbonyl group, and a polyethylene glycol (PEG); and/or the C-terminus of the peptide may be bound with any one protecting group selected from the group consisting of an amino group ($-NH_2$), a tertiary alkyl group, and an azide group ($-NHNH_2$). The peptide may optionally further include a targeting sequence, a tag, a labeled residue, or an amino acid prepared for a specific purpose of increasing half-life or peptide stability.

As used herein, the term "stability" may mean not only in vivo stability that protects the peptide from attack of protein cleavage enzymes in vivo, but also storage stability (e.g., room temperature storage stability).

Another aspect provides a cosmetic composition including the peptide including an amino acid sequence of SEQ ID NO: 1, SEQ ID NO: 2, or SEQ ID NO: 3 as an active ingredient; a pharmaceutical composition including the peptide including an amino acid sequence of SEQ ID NO: 1, SEQ ID NO: 2, or SEQ ID NO: 3 as an active ingredient; and use of the peptide including an amino acid sequence of SEQ ID NO: 1, SEQ ID NO: 2, or SEQ ID NO: 3 for the preparation of the cosmetic or pharmaceutical composition, or for being used as the cosmetic or pharmaceutical composition.

Still another aspect provides a skin-whitening composition including the peptide consisting of an amino acid sequence of SEQ ID NO: 1, SEQ ID NO: 2, or SEQ ID NO: 3 as an active ingredient.

Among the terms or elements mentioned in the description of the peptide, those the same as mentioned above are as described above.

As used herein, the term "skin whitening" may be interpreted to not only brighten skin tone by inhibiting the synthesis of melanin pigments, but also to improve skin hyperpigmentation caused by ultraviolet light, hormones, or heredity. Here, hyperpigmentation of the skin may include freckles, melasma, senile black spots, brown spots, lentigo, etc., but is not limited thereto.

As used herein, the term "improving" may mean all actions that at least reduce a parameter related to the condition being alleviated or treated, for example, the degree of a symptom.

Existing functional peptides, despite their effective biological activity, have disadvantages that they do not effectively enter target tissues or cells due to their own size or are cleared in the body in a short time due to the short half-life. In contrast, the whitening composition according to one embodiment includes the peptide consisting of 10 amino acids or less as an active ingredient, and therefore, the active ingredient has a very excellent skin penetration rate. For example, when topically applied to the skin, the composition may exhibit an effective skin whitening effect.

According to one embodiment, the peptide may significantly inhibit melanin production and tyrosinase activity. Further, the peptide may inhibit expression of Rab27a, Mlph, myosin VA, MITF, tyrosinase, or TRP1, which is a factor associated with melanin production. Therefore, the peptide may be used as an active ingredient of a skin-whitening cosmetic composition.

Still another aspect provides a skin-whitening cosmetic composition including the peptide consisting of an amino acid sequence of SEQ ID NO: 1, SEQ ID NO: 2, or SEQ ID NO: 3 as an active ingredient.

Among the terms or elements mentioned in the description of the peptide, those the same as mentioned above are as described above.

The cosmetic composition may include a cosmetically effective amount of the peptide; and/or a cosmetically acceptable carrier, but is not limited thereto.

As used herein, the term "cosmetically effective amount" means an amount sufficient to achieve the skin-whitening efficacy of the cosmetic composition.

A weight ratio of the peptide and the cosmetically acceptable carrier may be, for example, 500:1 to 1:500, and for example, the weight ratio may be 450:1 to 1:450, 400:1 to 1:400, 350:1 to 1:350, 300:1 to 1:300, 250:1 to 1:250, 200:1 to 1:200, 150:1 to 1:150, 100:1 to 1:100, 80:1 to 1:80, 60:1 to 1:60, 40:1 to 1:40, 20:1 to 1:20, 10:1 to 1:10, 8:1 to 1:8, 6:1 to 1:6, 4:1 to 1:4, or 2:1 to 1:2, but is not limited thereto.

The cosmetic composition may be prepared in any formulation commonly prepared in the art, and for example, may be formulated into a solution, a suspension, an emulsion, a paste, a gel, a cream, a lotion, a powder, a soap, a surfactant-containing cleanser, oil, a powder foundation, an emulsion foundation, a wax foundation, a spray, etc., but is not limited thereto. For example, the cosmetic composition may be prepared in the formulation of a softening lotion, a nutrition lotion, a nutrition cream, a massage cream, an essence, an eye cream, a cleansing cream, a cleansing foam, cleansing water, a pack, a spray, a powder, etc.

When the formulation of the cosmetic composition is a paste, cream, or gel, animal oil, vegetable oil, wax, paraffin, starch, tragacanth, a cellulose derivative, polyethylene glycol, silicone, bentonite, silica, talc, zinc oxide, etc. may be used as a carrier component.

When the formulation of the cosmetic composition is a powder or a spray, lactose, talc, silica, aluminum hydroxide, calcium silicate, or polyamide powder may be used as a carrier component. For example, in the case of a spray, a propellant such as chlorofluorohydrocarbon, propane/butane, or dimethyl ether may be additionally included.

When the formulation of the cosmetic composition is a solution or an emulsion, a solvent, a solubilizing agent, or an emulsifying agent may be used as a carrier component. For example, water, ethanol, isopropanol, ethyl carbonate, ethyl acetate, benzyl alcohol, benzyl benzoate, propylene glycol, 1,3-butylglycol oil, glycerol aliphatic ester, polyethyleneglycol, or fatty acid ester of sorbitan may be included.

When the formulation of the cosmetic composition is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, etc. may be used as a carrier component.

When the formulation of the cosmetic composition is a surfactant-containing cleanser, aliphatic alcohol sulfate, aliphatic alcohol ether sulfate, sulfosuccinic acid monoester, isethionate, an imidazolium derivative, methyltaurate, sarcosinate, fatty acid amide ether sulfate, alkylamidobetaine, aliphatic alcohol, fatty acid glyceride, fatty acid diethanolamide, vegetable oil, a lanolin derivative, ethoxylated glycerol fatty acid ester, etc. may be used as a carrier component.

In addition to the peptide as an active ingredient and the carrier component, the cosmetic composition may include ingredients commonly used in cosmetic compositions, for example, a common auxiliary agent such as an antioxidant, a stabilizer, a solubilizer, vitamins, a pigment, and a flavoring agent.

Still another aspect provides a method of whitening the skin, the method including applying, to the skin of an individual, the cosmetic composition including the peptide consisting of an amino acid sequence of SEQ ID NO: 1, SEQ ID NO: 2, or SEQ ID NO: 3 as an active ingredient.

Among the terms or elements mentioned in the description of the cosmetic composition, those the same as mentioned above are as described above.

As used herein, the terms "applying", "administering", and "spreading" may be used interchangeably, and may mean at least partial localization of the composition according to one embodiment to a desired site, or placement of the composition according to one embodiment into an individual via a route of administration.

Still another aspect provides a pharmaceutical composition for preventing or treating a melanin hyperpigmentation disease, the pharmaceutical composition including the peptide consisting of an amino acid sequence of SEQ ID NO: 1, SEQ ID NO: 2, or SEQ ID NO: 3 as an active ingredient.

Among the terms or elements mentioned in the description of the peptide, those the same as mentioned above are as described above.

As used herein, the term "preventing" refers to all actions that inhibit or slow down the onset of a disease by the administration of the composition.

As used herein, the term "treating" refers to any form of treatment that provides an individual suffering from or at risk of developing a disease with effects including improving conditions (e.g., one or more symptoms) of the individual, delaying disease progression, delaying the onset of symptoms, slowing of symptom progression, etc. Thus, the "treating" and "preventing" do not mean the curing or complete elimination of symptoms.

The term "individual" means a subject in need of treatment of a disease, and more specifically, a mammal, such as a human or non-human primate, a mouse, a dog, a cat, a horse, and a cow.

The "melanin hyperpigmentation disease", which is a disease to be prevented or treated by the pharmaceutical composition, may collectively refer to a disease in which melanin pigment is excessively produced and deposited on the skin. For example, the disease may be melasma, freckles, lentigo senilis, or solar lentigines, but is not limited thereto.

The pharmaceutical composition may include a pharmaceutically effective amount of the peptide and/or a pharmaceutically acceptable carrier, but is not limited thereto.

As used herein, the term "pharmaceutically effective amount" may mean an amount sufficient to achieve the efficacy of the pharmaceutical composition to prevent or treat a melanin hyperpigmentation disease.

A weight ratio of the peptide and the pharmaceutically acceptable carrier may be, for example, 450:1 to 1:450, 400:1 to 1:400, 350:1 to 1:350, 300:1 to 1:300, 250:1 to 1:250, 200:1 to 1:200, 150:1 to 1:150, 100:1 to 1:100, 80:1 to 1:80, 60:1 to 1:60, 40:1 to 1:40, 20:1 to 1:20, 10:1 to 1:10, 8:1 to 1:8, 6:1 to 1:6, 4:1 to 1:4, or 2:1 to 1:2, but is not limited thereto.

The pharmaceutically acceptable carrier is commonly used in the preparation, and may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but is not limited thereto. Appropriate pharmaceutically acceptable carriers and formulations are described in detail in Remington's Pharmaceutical Sciences (19th ed., 1995).

The pharmaceutical composition may further include a lubricant, a wetting agent, a sweetener, a flavoring agent, an emulsifier, a suspending agent, a preservative, etc., in addition to the above components, but is not limited thereto.

The pharmaceutical composition may be administered orally or parenterally, and specifically parenterally. The parenteral administration may include intramuscular injection, intravenous injection, subcutaneous injection, intraperitoneal injection, topical administration, transdermal administration, etc., but is not limited thereto.

An administration dose of the pharmaceutical composition may be 0.0001 µg to 1000 µg (microgram), 0.001 µg to 1000 µg, 0.01 µg to 1000 µg, 0.1 µg to 1000 µg, or 1.0 µg to 1000 µg per day, but is not limited thereto. The pharmaceutical composition may be prescribed in various ways depending on factors such as a formulation method, administration mode, a patient's age, weight, sex, disease conditions, food, administration time, administration route, excretion rate, and response sensitivity.

The pharmaceutical composition may be prepared in a unit dose form or may be prepared into a multidose container by formulating the pharmaceutical composition using a pharmaceutically acceptable carrier and/or excipient according to a method, which may be easily carried out by those skilled in the art to which the present disclosure pertains.

The formulation may be a solution, suspension, or emulsion form in an oil or aqueous medium, or may be an extract, powder, granule, tablet, or capsule form, and may further include a dispersing agent and/or a stabilizer.

Still another aspect provides a method of preventing or treating a melanin hyperpigmentation disease, the method including administering, to an individual, a therapeutically effective amount of the pharmaceutical composition including the peptide consisting of an amino acid sequence of SEQ ID NO: 1, SEQ ID NO: 2, or SEQ ID NO: 3 as an active ingredient.

Among the terms or elements mentioned in the description of the pharmaceutical composition, those the same as mentioned above are as described above.

Still another aspect provides a skin-whitening food composition including the peptide consisting of an amino acid sequence of SEQ ID NO: 1, SEQ ID NO: 2, or SEQ ID NO: 3 as an active ingredient.

Among the terms or elements mentioned in the description of the peptide, those the same as mentioned above are as described above.

Content of the peptide as an active ingredient in the food composition may be appropriately selected without limitation depending on the form of the food, use thereof, etc. For example, the peptide may be added in an amount of 0.01% by weight to 15% by weight, based on the total weight of the food. For example, the peptide may be added in a proportion of 0.02 g to 10 g, or 0.3 g to 1 g, based on 100 ml of a health drink composition.

Advantageous Effects of Disclosure

A peptide according to an aspect significantly inhibits melanin production and tyrosinase activity as well as expression of a factor associated with melanin production, thereby exhibiting excellent skin-whitening effects.

The peptide according to an aspect significantly inhibits melanin production and tyrosinase activity as well as expression of a factor associated with melanin production, thereby being applied in alleviating or improving a melanin hyperpigmentation disease in the skin.

Accordingly, the peptide according to an aspect may be applied as an active ingredient for a skin-whitening composition or a pharmaceutical composition for treating or preventing a melanin hyperpigmentation disease.

MODE OF DISCLOSURE

Hereinafter, the present disclosure will be described in more detail with reference to embodiments. However, these embodiments are for illustrative purposes only, and the scope of the present disclosure is limited to these embodiments.

Example 1. Synthesis of Peptide

A peptide having an amino acid sequence of SEQ ID NO: 1 described in the following [Table 1] was synthesized using an automated peptide synthesizer (Milligen 9050, Millipore, USA), and pure peptide was isolated using a C18 reversed phase high performance liquid chromatography (HPLC) (Waters Associates, USA). ACQUITY UPLC BEH300 C18 (2.1 mm×100 mm, 1.7 μm, Waters Co, USA) was used as a column.

TABLE 1

| SEQ ID NO: | Sequence (N-terminus to C-terminus) |
|---|---|
| 1 | LRKRKRRFWVL |
| 2 | FHFIPNW |
| 3 | WPFLRP |

Example 2. Examination of Inhibitory Effect on Melanin Production

A mouse melanoma cell B16F10 was seeded in a 6-well plate at a density of 5×10⁴ cells/well, followed by incubation for 16 hours. Thereafter, the culture medium was replaced by a medium supplemented with 2% serum, and then 200 ng/ml of α-melanocyte-stimulating hormones (α-MSH) was added thereto to stimulate melanin production, together with each peptide of an amino acid sequence of SEQ ID NO: 1, 2, or 3 at a concentration of 10 μM, 50 μM, 100 μM, or 200 μM, respectively, followed by incubation for 72 hours. Thereafter, the incubated cells were dissolved in 1 N NaOH, and absorbance at 450 nm was measured. Moreover, an untreated group (Con) was used as a control, and only an α-MSH-treated group as a negative control and a known skin-whitening agent Arbutin (200 μM, 500 μM) and an α-MSH-treated group as a positive control were used.

Figure 1:
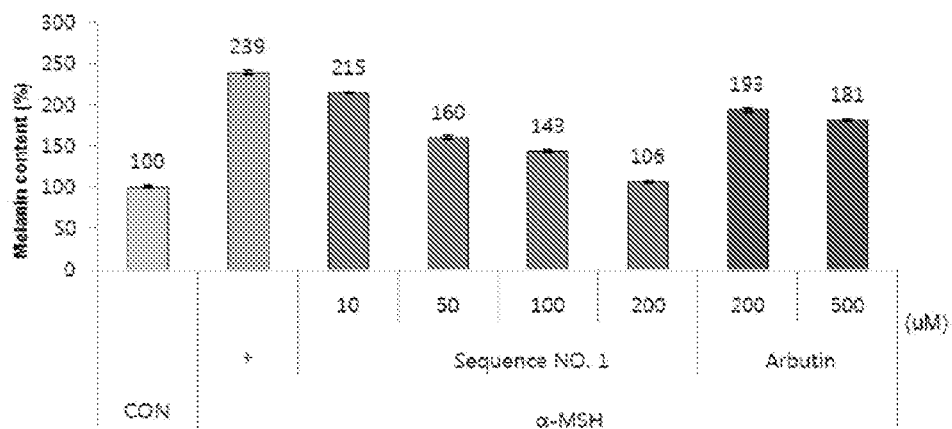
FIG. 1 shows results of examining reduction of melanin production, after adding a peptide consisting of an amino acid sequence of SEQ ID NO: 1 to B16F10 cells.
Figure 2:
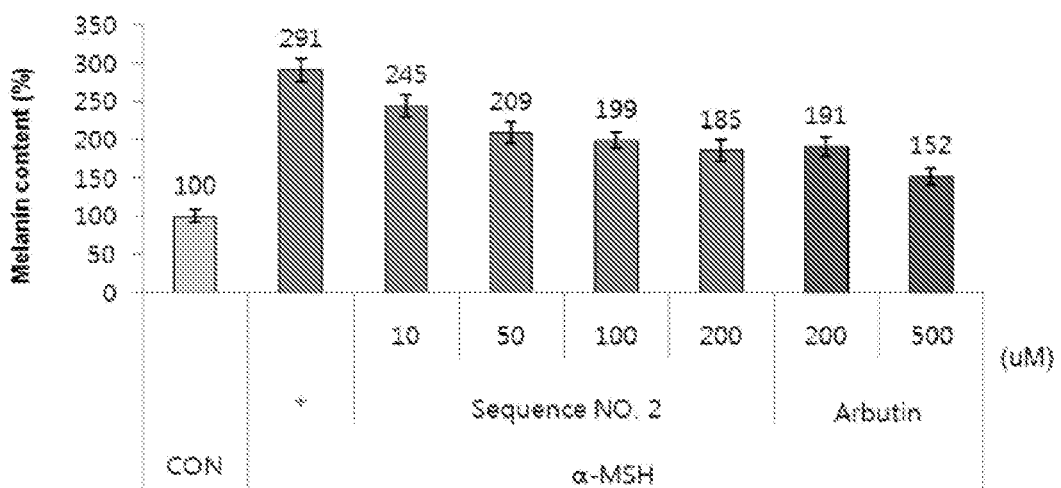
FIG. 2 shows results of examining reduction of melanin production, after adding a peptide consisting of an amino acid sequence of SEQ ID NO: 2 to B16F10 cells.
Figure 3:
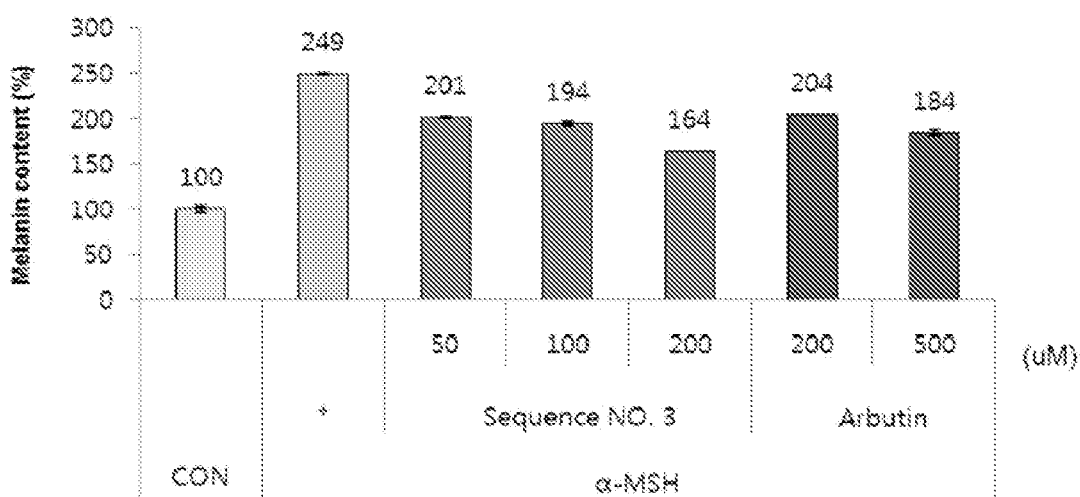
FIG. 3 shows results of examining reduction of melanin production, after adding a peptide consisting of an amino acid sequence of SEQ ID NO: 3 to B16F10 cells.

As a result, as shown in FIGS. 1 to 3, it was confirmed that melanin production was reduced in a concentration-dependent manner by addition of the peptide consisting of an amino acid sequence of SEQ ID NO: 1, 2, or 3.

Example 3. Examination of Inhibitory Effect on Tyrosinase Activity

A mouse melanoma cell B16F10 was seeded in a 6-well plate at a density of 5×10⁴ cells/well, followed by incubation for 16 hours. Thereafter, the culture medium was replaced by a medium supplemented with 2% serum, and then 200 ng/ml of α-MSH was added thereto, together with each peptide of an amino acid sequence of SEQ ID NO: 1, 2, or 3 at a concentration of 1 μM, 10 μM, 20 μM, 40 μM, 60 μM, 80 μM or 160 μM, respectively, followed by incubation for 72 hours. The 6-well plate was placed on ice, and then washed with cold PBS. The cells were lysed by adding a 0.1 M sodium phosphate buffer (pH 6.8, lysis buffer) containing 1% triton X-100. Thereafter, the cells in the well plate were scraped, and collected in a 1.5 ml tube, followed by vortexing. Centrifugation was carried out at 15,000 rpm for 10 minutes to obtain a supernatant. Thereafter, proteins in the supernatant was quantified to adjust the protein content at a predetermined amount. A buffer was added thereto, and total 90 μl of the sample was dispensed in a 96-well plate. Further, an experimental sample, a blank sample, and a positive control sample were prepared in the plate as shown in Table 2 below.

TABLE 2

| | Experimental sample | Blank sample | Positive control sample |
|---|---|---|---|
| Sample | 90 μl | — | — |
| Buffer | — | 90 μl | 90 μl |
| Mushroom tyrosinase (0.1 mg/ml) | — | — | 10 μl |

Thereafter, 20 μL of 10 mM L-DOPA was added to each sample, and incubated at 37° C. for 1 hour. Then, absorbance at 475 nm was measured. In addition, an untreated group (Con) was used as a control, and only α-MSH-treated group as a negative control and Arbutin (200 μM or 500 μM) and α-MSH-treated group as a positive control were used.

Figure 4:
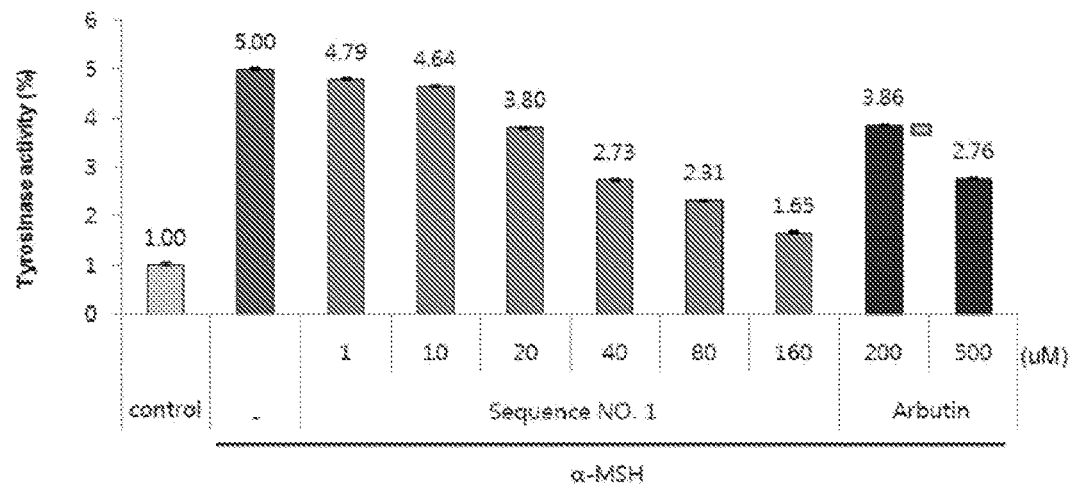
FIG. 4 shows results of examining reduction of tyrosinase activity, after adding the peptide consisting of the amino acid sequence of SEQ ID NO: 1 to B16F10 cells.
Figure 5:
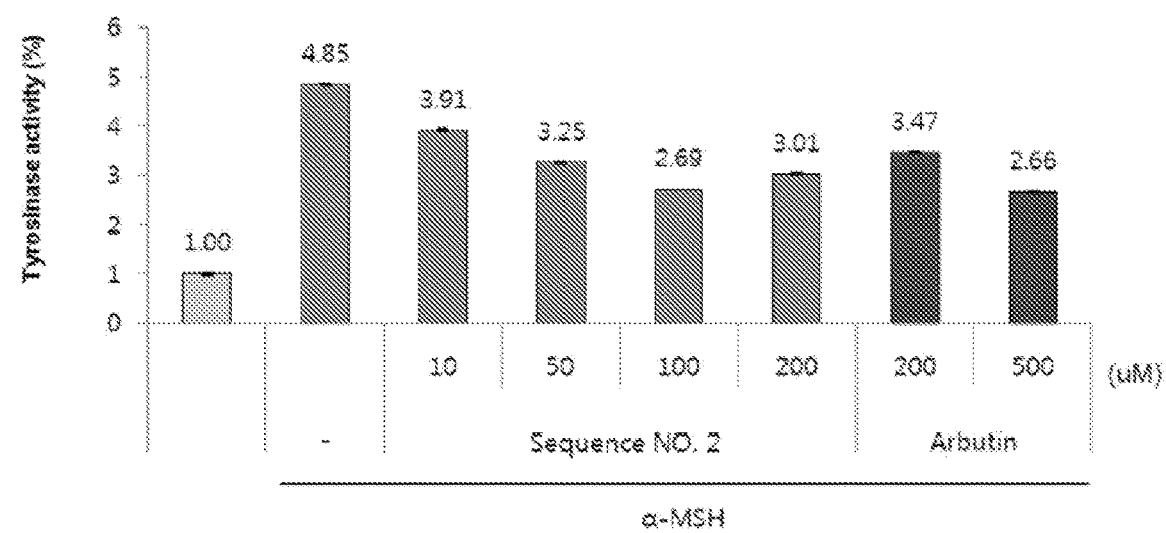
FIG. 5 shows results of examining reduction of tyrosinase activity, after adding the peptide consisting of the amino acid sequence of SEQ ID NO: 2 to B16F10 cells.
Figure 6:
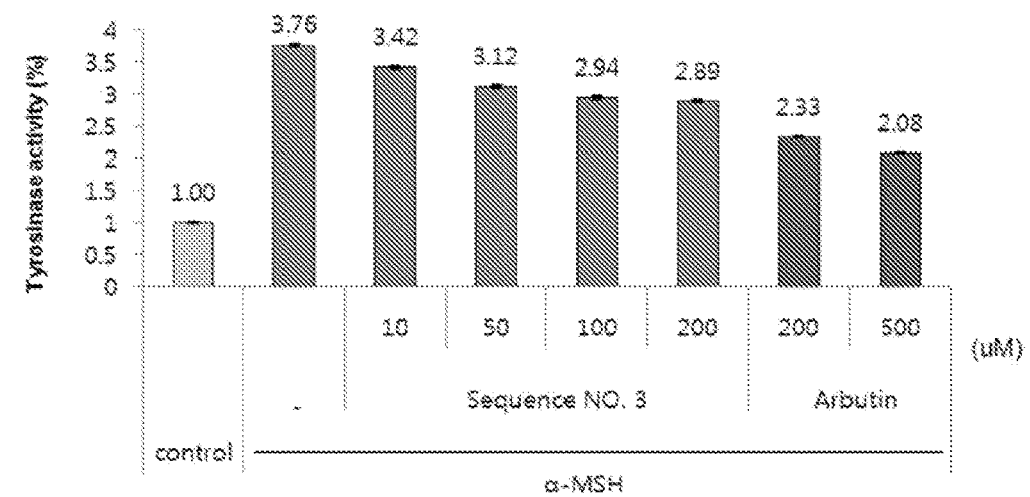
FIG. 6 shows results of examining reduction of tyrosinase activity, after adding the peptide consisting of the amino acid sequence of SEQ ID NO: 3 to B16F10 cells.

As a result, as shown in FIGS. 4 to 6, it was confirmed that tyrosinase activity was inhibited in a concentration-dependent manner by addition of the peptide consisting of an amino acid sequence of SEQ ID NO: 1, 2, or 3.

Example 4. Examination of Inhibitory Effect on Expression of Melanin Production-Associated Genes A mouse melanoma cell B16F10 was seeded in a 6-well plate at a density of 5×10$^4$ cells/well, followed by incubation for 16 hours. Thereafter, the culture medium was replaced by a medium supplemented with 2% serum, and then 200 ng/ml of α-MSH was added thereto, together with each peptide of an amino acid sequence of SEQ ID NO: 1, 2, or 3 at a concentration of 10 μM, 50 μM, 100 μM, or 200 μM, respectively, followed by incubation for 72 hours. mRNAs were extracted from the cultured cells, and the extracted mRNAs were reverse transcribed using a cDNA synthesis kit & PCR pre-mix (Intron, Korea), thereby synthesizing cDNA, respectively. Thereafter, a polymerase chain reaction (PCR) was carried out using each cDNA and Rab27a, Melanophilin (Mlph), myosin VA, MITF, Tyrosinase, and TRP1 primers. Moreover, a control, a negative control, and a positive control were used in the same manner as in Example 2, and nucleotide sequences of the primers used herein are the same as in Table 3 below.

TABLE 3

| Name of primer | | Sequence (5'->3') | SEQ ID NO: |
|---|---|---|---|
| Rab27a | forward | GAAAATAGCGCCAAGCACCC | 4 |
| | reverse | CCTCTTTCACTGCCCTCTGG | 5 |
| Mlph | forward | ACGATGTCAGGGGCAAACAT | 6 |
| | reverse | CTCCTCTGTGTCAGCACTGG | 7 |
| myosin VA | forward | TTCTACATTGTGGGCGCCAT | 8 |
| | reverse | TCCTCCAGGTTGGTCAATCG | 9 |
| MITF | forward | CCAGCCTGGCGATCATGTCAT | 10 |
| | reverse | GGTCTGGACAGGAGTTGCTG | 11 |
| Tyrosinase | forward | GGCCAGCTTTCAGGCAGAGG | 12 |
| | reverse | TGGTGCTTCATGGGCAAAAT | 13 |
| TRP1 | forward | TCTGTGAAGGTGTGCAGGAG | 14 |
| | reverse | CCGAAACAGAGTGGAAGGTT | 15 |
| GAPDH | forward | GGTGTGAACGGATTTGGCCGTATTG | 16 |
| | reverse | CCGTTGAATTTGCCGTGAGTGGAGT | 17 |

Figure 7:
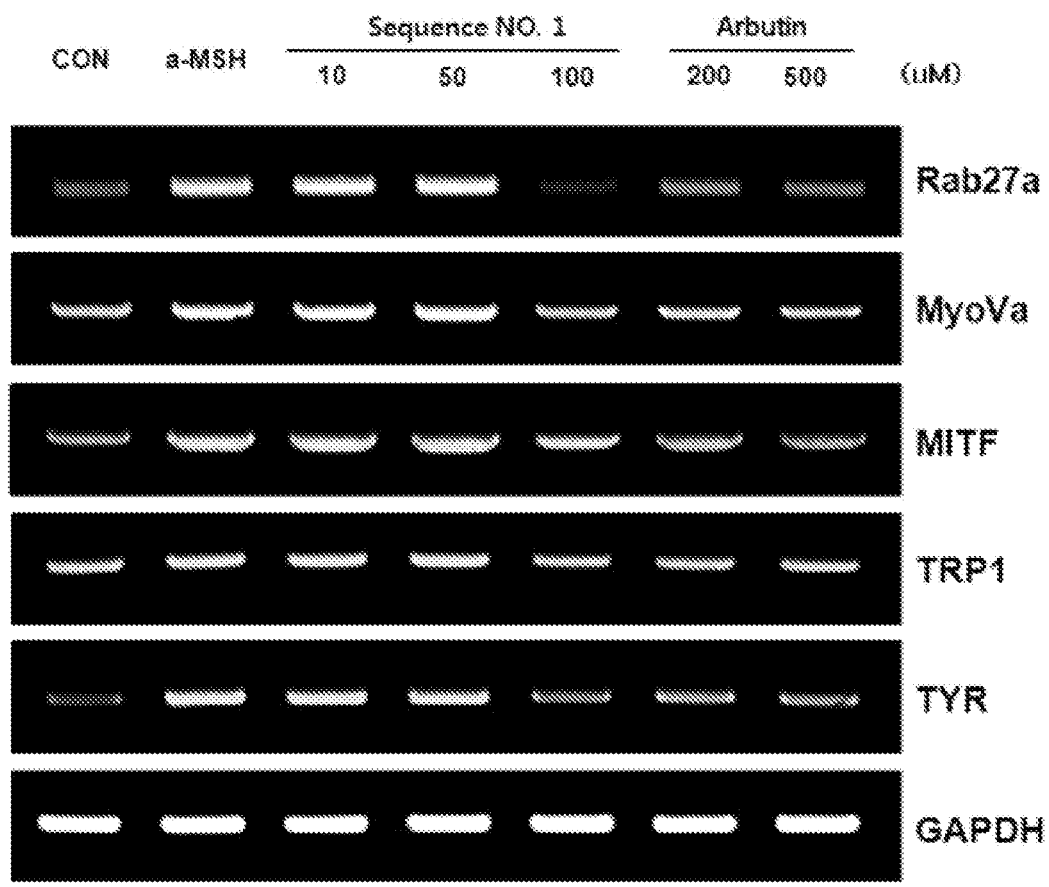
FIG. 7 shows results of examining inhibition of expression of Rab27a, myosin VA, MITF, TRP1, and tyrosinase, which are genes associated with melanin production, after adding the peptide consisting of the amino acid sequence of SEQ ID NO: 1 to B16F10 cells.
Figure 8:
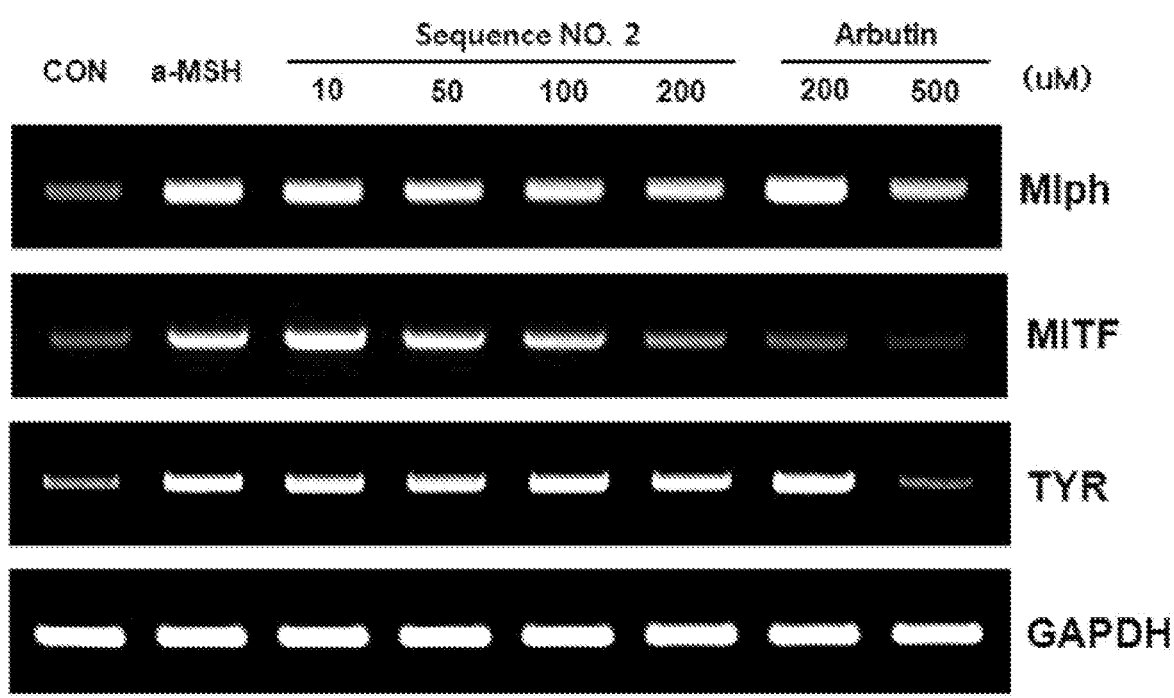
FIG. 8 shows results of examining inhibition of expression of Mlph, MITF, and tyrosinase, which are genes associated with melanin production, after adding the peptide consisting of the amino acid sequence of SEQ ID NO: 2 to B16F10 cells.
Figure 9:
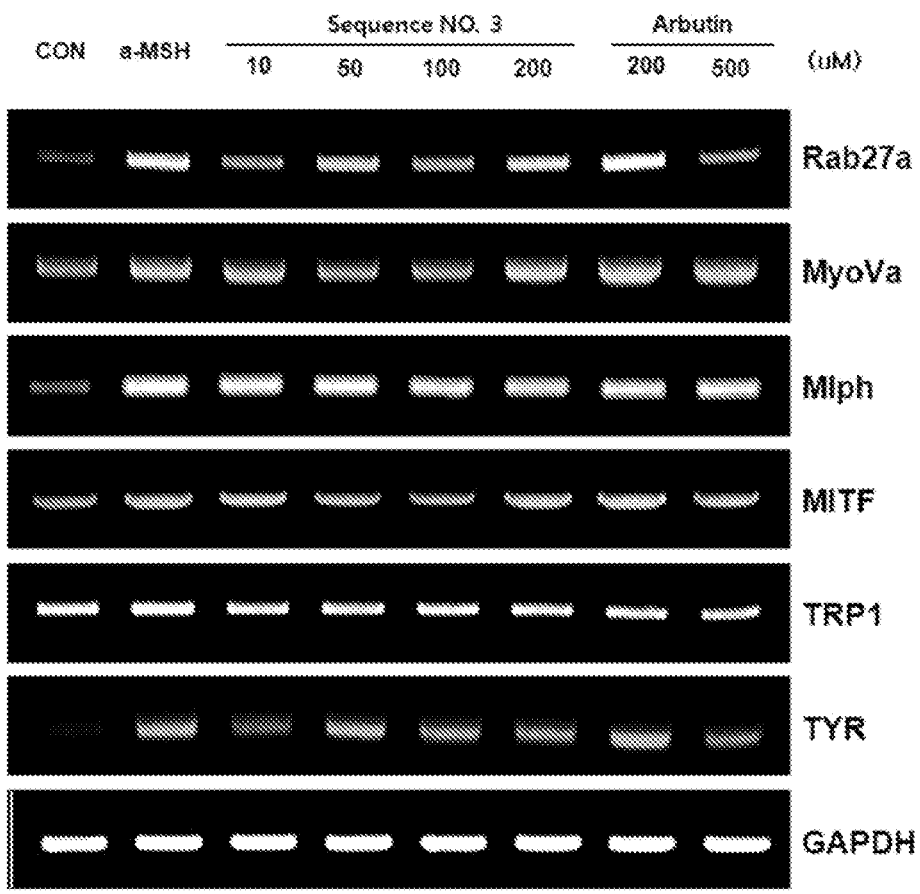
FIG. 9 shows results of examining inhibition of expression of Rab27a, myosin VA, Mlph, MITF, tyrosinase, and TRP1, which are genes associated with melanin production, after adding the peptide consisting of the amino acid sequence of SEQ ID NO: 3 to B16F10 cells.

As a result, as shown in FIG. 7, it was confirmed that expression of Rab27a, myosin VA, MITF, TRP1, and tyrosinase, which are melanin production-associated genes, was inhibited by addition of the peptide consisting of the amino acid sequence of SEQ ID NO: 1. Further, as shown in FIG. 8, it was confirmed that expression of Mlph, MITF, and tyrosinase, which are melanin production-associated genes, was inhibited by addition of the peptide consisting of the amino acid sequence of SEQ ID NO: 2. Furthermore, as shown in FIG. 9, it was confirmed that expression of Rab27a, myosin VA, Mlph, MITF, Tyrosinase, and TRP1, which are melanin production-associated genes, was inhibited by addition of the peptide consisting of the amino acid sequence of SEQ ID NO: 3.

Example 5. Examination of Inhibitory Effect on Expression of Melanin Production-Associated Protein A mouse melanoma cell B16F10 was seeded in a 6-well plate at a density of 5×10$^4$ cells/well, followed by incubation for 16 hours. Thereafter, the culture medium was replaced by a medium supplemented with 2% serum, and then 200 ng/ml of α-MSH was added thereto, together with each peptide of an amino acid sequence of SEQ ID NO: 1, 2, or 3 at a concentration of 10 μM, 50 μM, 100 μM, or 200 μM, respectively, followed by incubation for 72 hours. Thereafter, the cultured cells were lysed, and then subjected to Western blotting using antibodies (santacruz biotechnology, USA) against Mlph, Rab27a, Tyrosinase, MITF, and TRP-1. In addition, a control, a negative control, and a positive control were used in the same manner as in Example 2.

Figure 10:
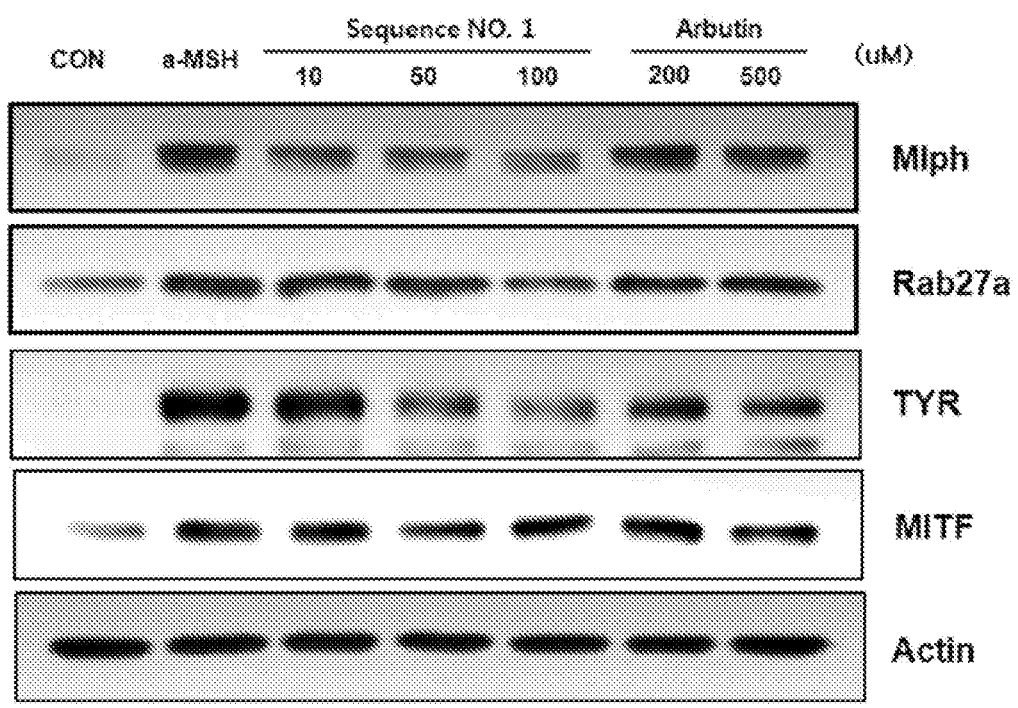
FIG. 10 shows results of examining inhibition of expression of Mlph, tyrosinase, and MITF, which are proteins associated with melanin production, after adding the peptide consisting of the amino acid sequence of SEQ ID NO: 1 to B16F10 cells.
Figure 11:
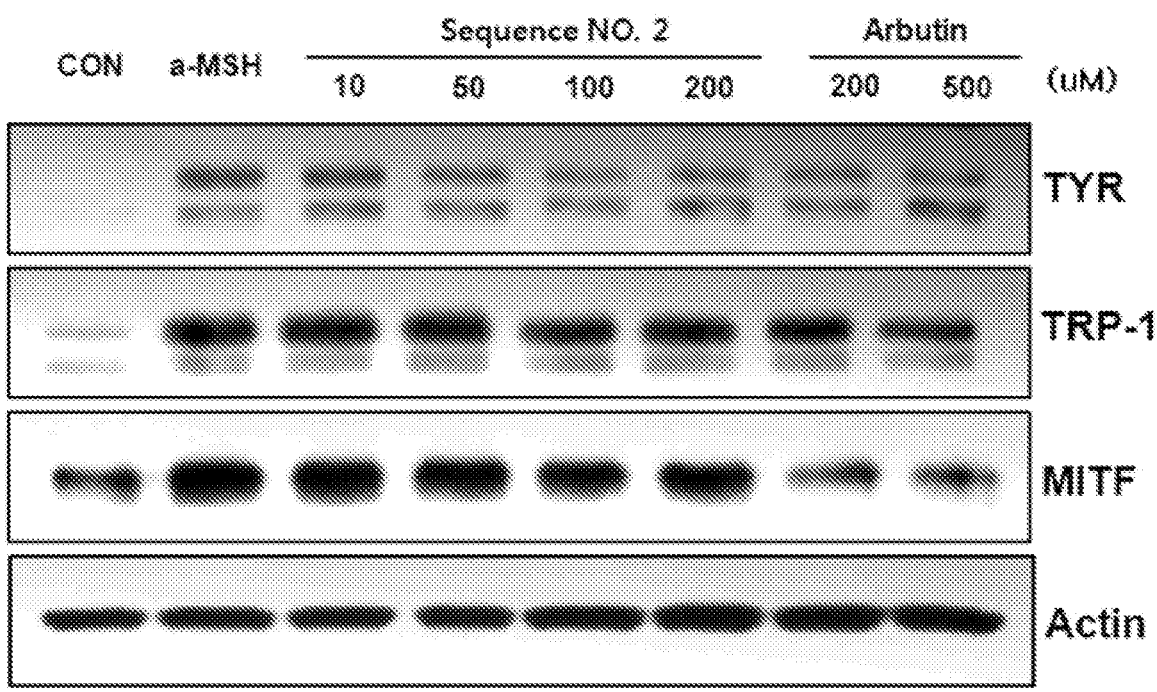
FIG. 11 shows results of examining inhibition of expression of tyrosinase, TRP-1, and MITF, which are proteins associated with melanin production, after adding the peptide consisting of the amino acid sequence of SEQ ID NO: 2 to B16F10 cells.
Figure 12:
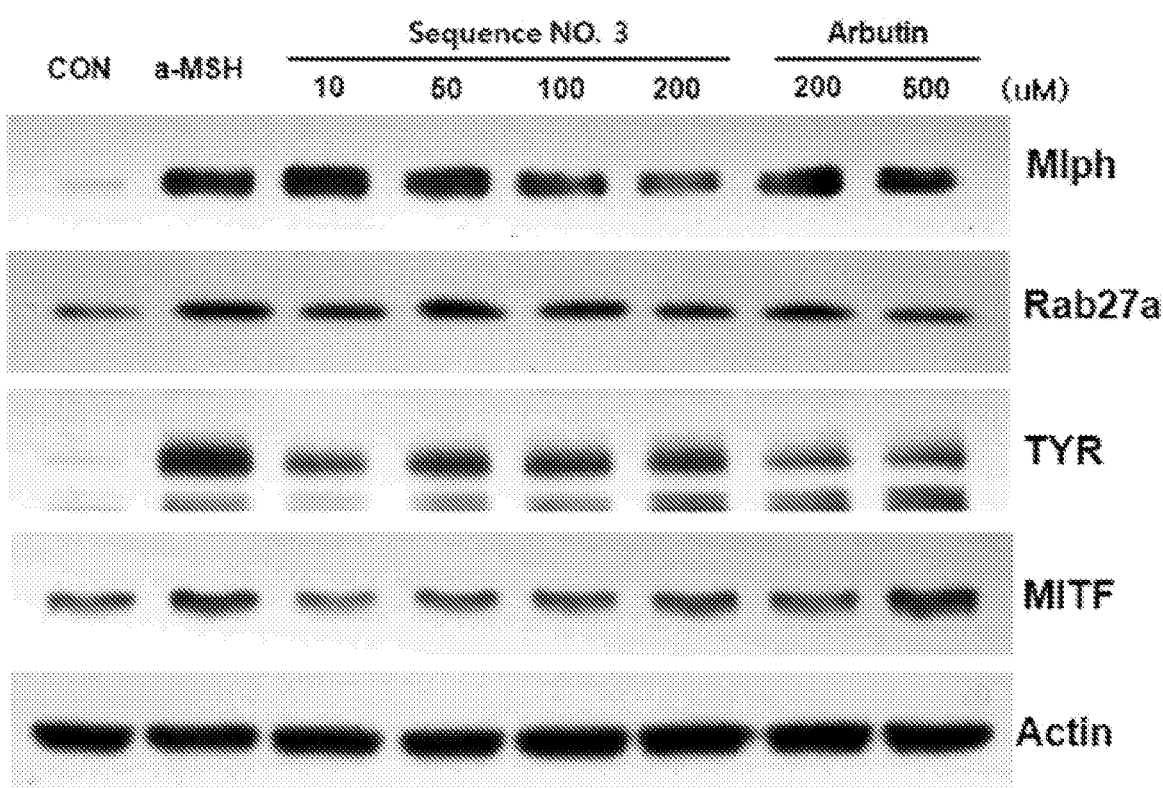
FIG. 12 shows results of examining inhibition of expression of Mlph, Rab27a, tyrosinase, and MITF, which are proteins associated with melanin production, after adding the peptide consisting of the amino acid sequence of SEQ ID NO: 3 to B16F10 cells.

As a result, as shown in FIG. 10, it was confirmed that expression of Mlph, Rab27a, Tyrosinase, and MITF, which are melanin production-associated proteins, was inhibited by addition of the peptide consisting of the amino acid sequence of SEQ ID NO: 1. Further, as shown in FIG. 11, it was confirmed that expression of Tyrosinase, TRP-1, and MITF, which are melanin production-associated proteins, was inhibited by addition of the peptide consisting of the amino acid sequence of SEQ ID NO: 2. Furthermore, as shown in FIG. 12, it was confirmed that expression of Mlph, Rab27a, Tyrosinase, and MITF, which are melanin production-associated proteins, was inhibited by addition of the peptide consisting of the amino acid sequence of SEQ ID NO: 3.

Taken together, the above experimental results indicate that the peptide consisting of the amino acid sequence of SEQ ID NO: 1, 2, or 3 according to one embodiment has skin-whitening efficacy.

The foregoing description of the present disclosure is only for illustrating, and those skilled in the art to which the present disclosure pertains will appreciate that the present disclosure may be easily modified in other specific forms without changing the technical spirit or essential characteristics thereof. Therefore, it should be understood that the above embodiments are not limitative, but illustrative in all aspects.

The invention claimed is:

1. A peptide consisting of the amino acid sequence of SEQ ID NO: 1, SEQ ID NO: 2, or SEQ ID NO: 3, optionally wherein the N- or C-terminus of the peptide is modified, wherein the peptide exhibits any one or more characteristic selected from the group consisting of:
(a) inhibition of melanin production;
(b) inhibition of tyrosinase activity; and
(c) inhibition of Ras-related protein Rab-27a (Rab27a), Melanophilin (Mlph), Myosin Heavy chain 12 (myosin VA), Melanocyte Inducing Transcription Factor (MITF), tyrosinase, or Tyrosinase Related Protein-1 (TRP1) expression.

2. The peptide of claim 1, wherein the N-terminus of the peptide is bound with any one protecting group selected from the group consisting of an acetyl group, a fluoreonyl-methoxycarbonyl group, a formyl group, a palmitoyl group, a myristyl group, a stearyl group, a butoxycarbonyl group, an allyloxycarbonyl group, and a polyethylene glycol (PEG).

3. The peptide of claim 1, wherein the C-terminus of the peptide is bound with any one protecting group selected from the group consisting of an amino group (—NH$_2$), a tertiary alkyl group, and an azide group (—NHNH$_2$).

4. A skin-whitening composition comprising the peptide of claim 1 as an active ingredient.

5. A cosmetic composition comprising the skin-whitening composition of claim 4.

6. A pharmaceutical composition for treating a melanin hyperpigmentation disease, the pharmaceutical composition comprising the skin-whitening composition of claim 5.

7. The pharmaceutical composition of claim 6, wherein the melanin hyperpigmentation disease is melasma, freckles, lentigo senilis, or solar lentigines.

8. A skin-whitening composition comprising the peptide of claim 2 as an active ingredient.

9. A cosmetic composition comprising the skin-whitening composition of claim 8.

10. A pharmaceutical composition for treating a melanin hyperpigmentation disease, the pharmaceutical composition comprising the skin-whitening composition of claim 8.

11. The pharmaceutical composition of claim 10, wherein the melanin hyperpigmentation disease is melasma, freckles, lentigo senilis, or solar lentigines.

12. A skin-whitening composition comprising the peptide of claim 3 as an active ingredient.

13. A cosmetic composition comprising the skin-whitening composition of claim 12.

14. A pharmaceutical composition for treating a melanin hyperpigmentation disease, the pharmaceutical composition comprising the skin-whitening composition of claim 12.

15. The pharmaceutical composition of claim 14, wherein the melanin hyperpigmentation disease is melasma, freckles, lentigo senilis, or solar lentigines.

16. A peptide consisting of the amino acid sequence of SEQ ID NO: 1, SEQ ID NO: 2, or SEQ ID NO: 3, wherein the N- or C-terminus of the peptide is modified.

17. A method of whitening the skin, the method comprising applying, to the skin of an individual, the cosmetic composition of claim 5.

18. A method of treating a melanin hyperpigmentation disease, the method comprising administering, to an individual, a therapeutically effective amount of the pharmaceutical composition of claim 6.

* * * * *

SEQUENCE LISTING

```
<160> NUMBER OF SEQ ID NOS: 17

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Leu Arg Lys Arg Lys Arg Arg Phe Trp Val Leu
```

```
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Phe His Phe Ile Pro Asn Trp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Trp Pro Phe Leu Arg Pro
1               5

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gaaaatagcg ccaagcaccc                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cctctttcac tgccctctgg                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
acgatgtcag gggcaaacat                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ctcctctgtg tcagcactgg                                           20

<210> SEQ ID NO 8
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 8
ttctacattg tgggcgccat                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tcctccaggt tggtcaatcg                                               20

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
ccagcctggc gatcatgtca t                                             21

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ggtctggaca ggagttgctg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ggccagcttt caggcagagg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
tggtgcttca tgggcaaaat                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
```

```
tctgtgaagg tgtgcaggag                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ccgaaacaga gtggaaggtt                                              20

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
ggtgtgaacg gatttggccg tattg                                        25

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
ccgttgaatt tgccgtgagt ggagt                                        25
```